United States Patent
Kemnitz et al.

(10) Patent No.: US 7,592,287 B2
(45) Date of Patent: Sep. 22, 2009

(54) METHOD FOR THE PREPARATION OF HIGH SURFACE AREA METAL FLUORIDES

(75) Inventors: Erhard Kemnitz, Berlin (DE); Udo Gross, Berlin (DE); Stephan Ruediger, Rangsdorf (DE)

(73) Assignee: Humboldt-Universitaet Zu Berlin (DE)

( * ) Notice: Subject to any disclaimer, the term of this patent is extended or adjusted under 35 U.S.C. 154(b) by 164 days.

(21) Appl. No.: 10/541,612

(22) PCT Filed: Jan. 7, 2004

(86) PCT No.: PCT/EP2004/000049

§ 371 (c)(1), (2), (4) Date: Jul. 7, 2005

(87) PCT Pub. No.: WO2004/060806

PCT Pub. Date: Jul. 22, 2004

(65) Prior Publication Data

US 2006/0052649 A1 Mar. 9, 2006

Related U.S. Application Data

(60) Provisional application No. 60/438,308, filed on Jan. 7, 2003.

(30) Foreign Application Priority Data

Jan. 7, 2003 (EP) ................. 030000221
Mar. 25, 2003 (EP) ................. 030006656

(51) Int. Cl.
| | |
|---|---|
| *B01J 27/06* | (2006.01) |
| *B01J 27/122* | (2006.01) |
| *B01J 27/138* | (2006.01) |
| *B01J 27/132* | (2006.01) |
| *B01J 27/135* | (2006.01) |
| *C01B 9/08* | (2006.01) |
| *C01B 9/00* | (2006.01) |
| *C01G 23/02* | (2006.01) |
| *C01G 19/08* | (2006.01) |
| *C01G 49/10* | (2006.01) |
| *C01G 15/00* | (2006.01) |
| *C01F 3/00* | (2006.01) |
| *C01F 7/48* | (2006.01) |

(52) U.S. Cl. ............ 502/224; 502/225; 502/226; 502/228; 502/231; 423/489; 423/491; 423/492; 423/493; 423/494; 423/495

(58) Field of Classification Search ......... 502/224–226, 502/228, 231; 423/489, 491–495
See application file for complete search history.

(56) References Cited

U.S. PATENT DOCUMENTS 2,959,557 A * 11/1960 Hansford ............ 502/227

(Continued)

FOREIGN PATENT DOCUMENTS

| FR | 1383927 A | 1/1965 |
|---|---|---|
| GB | 995 186 A | 6/1965 |

OTHER PUBLICATIONS

Delattre et al., "Plasma-Fluorination Synthesis of High Surface Area Aluminum Trifluoride from a Zeolite Precursor", Journal of the American Chemical Society, vol. 123, 2001, pp. 5364-5365.

*Primary Examiner*—Patricia L Hailey
(74) *Attorney, Agent, or Firm*—Rothwell, Figg, Ernst & Manbeck, p.c.

(57) ABSTRACT

The present invention is related to a method for preparing an amorphous metal fluoride of the formula $M^{x+}F_{x-\delta}$ comprising the steps of
a) providing a precursor, whereby the precursor comprises a structure having a formula of $M^{x+}F_{(x-\delta)-y}B_y$; and
b) reacting the precursor with a fluorinating agent generating the amorphous metal flouride having a formula of $M^{x+}F_{x-\delta}$,
whereby M is selected from the group comprising metals of the second, third and fourth main group and any subgroup of the periodic table,
B is a coordinately bound group;
x is any integer of 2 or 3;
y is any integer between 1 and 3;
$\delta$ is 0 to 0.1; and
$x-\delta > y$.

26 Claims, 2 Drawing Sheets

U.S. PATENT DOCUMENTS

| | | | | |
|---|---|---|---|---|
| 3,294,852 A | * | 12/1966 | Vecchio et al. | 570/169 |
| 3,644,545 A | * | 2/1972 | Buckman | 570/168 |
| 4,275,046 A | * | 6/1981 | McVicker et al. | 423/258 |
| 4,798,818 A | * | 1/1989 | Baizer et al. | 502/228 |
| 5,051,278 A | * | 9/1991 | Paz-Pujalt | 427/108 |
| 5,271,956 A | * | 12/1993 | Paz-Pujalt | 427/108 |
| 5,277,889 A | * | 1/1994 | Power et al. | 423/491 |
| 5,342,809 A | * | 8/1994 | Poulain et al. | 501/12 |

\* cited by examiner

METHOD FOR THE PREPARATION OF HIGH SURFACE AREA METAL FLUORIDES

CROSS REFERENCE TO RELATED APPLICATION

This application is a 35 USC § 371 National Phase Entry Application from PCT/EP2004/000049 filed Jan. 7, 2004, and designating the United States which claims the benefit of U.S. Provisional 60/438,308, filed Jan. 7, 2003.

The present invention is related to a method for preparing an amorphous metal fluoride, a catalyst comprising an amorphous metal fluoride, a method for preparing such catalyst and uses of said catalyst.

Metal oxides and metal fluorides are of great importance to the chemical, pharmaceutical and, e.g., ceramics industry. In particular, inorganic materials having high surface areas are of great interest for, e.g., heterogeneous catalysis where the activity of a catalyst depends largely on its surface. Metal oxides with very high surface areas can be prepared via sol-gel routes, by freeze-drying or under supercritical conditions as xerogels (c. f. Advanced Catalysts and Nanostructured Materials, editor W. R. Moser: Chapter 2—The Role of Prehydrolysis in the Preparation of Zr—Si Aerogels by J. B. Miller and E. I. Ko, Academic Press, San Diego, 1996) or aerogels. The manufacture of metal fluorides used as thin film coating prepared on a quartz base material is described in Choi, J.-B. et al., J. Korean Ind. Eng. Chem., Vol. 11, No. 8, November 2000, 969-973. In the process of manufacturing said metal fluorides, more particularly magnesium fluoride, a mixture of magnesium methoxide is admixed with a water containing solution of hydrogen fluoride and methanol.

A particularly preferred metal catalyst is aluminium trifluoride which is used as a Lewis acidic catalyst for industrial fluorination. The synthesis, characteristics and uses of such aluminium fluorides are described in E. Kemnitz and D.-H. Menz, Prog. Solid St. Chem. 26 (1998), p. 97-153.

Aluminium fluoride based catalysts such as $AlF_3$ exhibit an octahedral arrangement of fluorine atoms, the aluminium atoms of which are thus saturated in a coordinative manner. Because of this arrangement these $AlF_3$ species exhibit a comparatively low Lewis acidity. In addition, the crystalline structure goes along with a limited specific surface of e.g., 0.5 to 30 $m^2/g$ which is disadvantageous as the activity of a solid phase or heterogeneous catalyst strongly depends on its specific surface area Aluminium fluorides can be produced using wet-chemical synthesis and subsequent controlled dehydration. Alternatively, non-wet-chemical synthesis routes are reported. Ziegler, K. and Köster, R., Liebigs Ann. Chem. 608 (1957) 1-7 describe the synthesis of aluminium trifluoride using aluiminium trialkyl and boron trifluoride as starting materials. DE 4041771 describes the fluorination of aluminium chloride using anhydrous hydrogen fluoride. U.S. Pat. No. 5,157,171 discloses the fluorination of $AlCl_3$ using chlorofluorocarbons. Both methods result in an $AlCl_xF_{3-x}$ which still contains chlorine. This residual chlorine is responsible for both the observed high acidity and the high hygroscopicity. The product resulting from both methods is also referred to as aluminium chlorofluoride, ACF. Because of its hygroscopicity ACF is extremely difficult to be used in technical applications. Also, ACF is rapidly deactivated upon, e.g., contacting H containing organic solvents such as ethers, alcohols and the like. In addition, the particular fluorination process cannot be transferred to other metal chlorides as only the particular reaction provides the gain in energy required for the conversion of $AlCl_3$ into $AlF_3$.

The basic considerations in relation to and the limitations of metal fluoride catalysts as described above, also apply for doped metal fluoride catalysts. Doped metal fluoride catalysts can be particularly advantageous as it is known that in metal oxide as well as metal fluoride based catalysts a partial replacement of host metal atoms by doping metal atoms has a strong influence on the activity and/or selectivity of the respective catalyst. The manufacture of this kind of doped catalyst starts either from the solid host compound which is subsequently impregnated with the desired amount of a solution of the doping compound and subsequently dried and calcined at elevated temperatures. Alternatively, a solution is used in which both compounds, i.e. the host compound as well as the guest compound, are present at the desired ratio whereupon both compounds are co-precipitated, dried and subsequently calcined. The resulting catalyst product has always an activity limiting small surface area.

A further method for the manufacture of aluminium trifluoride is described by Delattre, J. L. et al., J. Am. Chem. Soc. 2001, 123, p. 5364-5, where a zeolite is fluorinated by an $NF_3$-plasma whereupon silicon concomitantly is removed from the solid alumo-zeolite. The thus obtained aluminium fluoride has a specific surface area of up to 190 $m^2/g$. However, the particular etching technology is not applicable to a large scale, i.e. industrial, catalyst production line.

The problem underlying the present invention is thus to provide a method for preparing an amorphous metal fluoride having a high active surface and preferably being catalytically active. It is a further problem underlying the present invention to provide a metal fluoride based catalyst which has a high specific surface and is moisture resistant, i.e. it may be handled in open air without becoming irreversibly deactivated.

According to the present invention the problem is solved in a first aspect by a method for preparing an amorphous metal fluoride of the formula $M^{x+}F_{x-\delta}$ comprising the steps of
a) providing a precursor, whereby the precursor comprises a structure having a formula of $M^{x+}F_{(x-\delta)-y}B_y$; and
b) reacting the precursor with a fluorinating agent generating the amorphous metal fluoride having a formula of $M^{x+}F_{x-\delta}$, whereby
 M is selected from the group comprising metals of the second, third and fourth main group and any subgroup of the periodic table,
 B is a coordinately bound group;
 x is any integer of 2 or 3;
 y is any integer between 1 and 3;
 δ is 0 to 0.1; and
 x−δ>y.

In an embodiment of the method B is selected from the group comprising alkoxides, enolates and salts of carboxylic acid. Preferably, the alkoxides, enolates or the carboxylic acid has a length of 1 to 5 C atoms.

In a further embodiment of the method B is an alkoxide having a formula of wherein c is any integer from 1 to 6. In a preferred embodiment c is any integer from 1 to 3.

In a still further embodiment of the method the precursor, any of the starting material for the precursor or the fluorinating agent is present in or introduced into an anhydrous organic solvent, whereby the anhydrous organic solvent is preferably selected from the group comprising alcohols, ethers, ketones, alkanes, formic acid, acidic acid and propionic acid.

In another embodiment of the method the precursor contains or is made from a compound of the Formula whereby
M, F, x, y, δ and B are as defined herein;
L is a solvent, preferably an anhydrous organic solvent as specified above; and
d is $\leq 1$.

In a preferred embodiment of the method step b is carried out at a temperature below the crystallisation point of the amorphous metal fluoride.

In an embodiment of the method the precursor is prepared by
providing the metal component of the precursor as an anhydrous metal compound, preferably as $M^{x+}B_x$,
with M, B and x being as defined herein, and
reacting said metal component with anhydrous hydrogen fluoride.

In another embodiment of the method the fluorinating agent is $CH_gCl_hF_{4-g-h}$ with the sum of g+h being equivalent to 1 to 3.

In a further embodiment of the method the precursor is reacted with $CH_gCl_hF_{4-g-h}$ at a temperature below the crystallisation point of the metal fluoride.

In a further embodiment of the method the precursor is reacted with gaseous hydrogen fluoride.

In a still further embodiment of the method the precursor contains less than 1.5 mole of any organic compound(s).

In a preferred embodiment of the method the amorphous metal fluoride is a catalyst, preferably a heterogenous catalyst.

According to the present invention the problem is solved in a second aspect by a method for the manufacture of a catalyst, preferably a catalyst comprising amorphous metal fluoride of the formula $M^{x+}F_{x-\delta}$, whereby
M is selected from the group comprising metals of the second, third and fourth main group and any subgroup of the periodic table,
x is any integer of 2 or 3; and
δ is 0.1,
comprising the steps of the method according to the first aspect of the present invention, wherein the amorphous metal fluoride is the catalyst.

According to the present invention the problem is solved in a third aspect by an amorphous metal fluoride obtainable by a method according to the first or second aspect of the present invention.

According to the present invention the problem is solved in a fourth aspect by a catalyst obtainable by a method according to the first or second aspect of the present invention.

According to the present invention the problem is solved in a fifth aspect by a catalyst comprising amorphous metal fluoride of the formula $M^{x+}F_{x-\delta}$, whereby
M is selected from the group comprising metals of the second, third and fourth main group and any subgroup of the periodic table,
x is any integer of 2 or 3; and
δ is 0 to 0.1,
which is catalytically active and preferably having an active surface of about 100-300 m²/g, preferably 180-280 m²/g.

In an embodiment of the catalyst according to the fourth and fifth aspect of the present invention the catalyst is a strong Lewis acid.

According to the present invention the problem is solved in a sixth aspect by an industrially producible catalyst, preferably a catalyst according to the fourth or fifth aspect of the present invention, containing amorphous metal fluoride of the formula $M^{x+}F_{x-\delta}$.

whereby
M is selected from the group comprising metals of the second, third and fourth main group and any subgroup of the periodic table,
x is any integer of 2 or 3, and
δ is 0 to 0.1,
being catalytically active and preferably having an active surface of about 100-300 m²/g, preferably 180-280 m²/g.

According to the present invention the problem is solved in a seventh aspect by a moisture resistant catalyst, preferably a catalyst according to the fourth to sixth aspect of the present invention, containing amorphous metal fluoride of the formula $M^{x+F}_{x-\delta}$.

whereby
M is selected from the group comprising metals of the second, third and fourth main group and any subgroup of the periodic table,
x is any integer of 2 or 3, and
δ is 0 to 0.1.

In an embodiment of the catalyst according to the fourth to seventh aspect of the present invention M is selected from the group comprising Zn, Sn, Cu, Fe, Cr, V, Mg and Al, whereby preferably M has a charge of +2 or +3.

In a preferred embodiment M is selected from the group comprising Mg and Al, whereby Mg preferably has a charge of +2 and Al preferably has a charge of +3.

In an embodiment of the catalyst according to the fourth to seventh aspect of the present invention $M^{x+}F_{x-\delta}$ is amorphous $AlF_3$ and is characterized either by
a) an Al-chemical shift of δ=−12.5 to −14.5 ppm, preferably δ=−13.8 ppm, or
b) an Al-quadrupole coupling constant QCC of about 1.5 MHz.

In an embodiment of the catalyst according to the fourth to seventh aspect of the present invention any of M is used as $M^{x+}F_{x-\delta}$, as guest component or as host component.

In another embodiment of the catalyst according to the fourth to seventh aspect of the present invention the catalyst contains less than 0.5 mole of organic compounds, preferably less than 0.1 mole of organic compounds.

In a preferred embodiment of the catalyst according to the fourth to seventh aspect of the present invention the catalyst is a heterogeneous catalyst and/or a doped catalyst.

In another embodiment of the catalyst according to the fourth to seventh aspect of the present invention the catalytically active compound $M^{x+}F_{x-\delta}$ is $FeF_3$ or $AlF_3$, further comprising $MgF_2$ as inert support material, whereby preferably the support material is doped with $AlF_3$ or $FeF_3$ to an extent of 1-45%, more preferable 5-25%, and most preferable 15-20%.

According to the present invention the problem is solved in an eigth aspect by a catalyst containing a metal fluoride of the formula $M^{x+}F_{x-\delta}$.

whereby
M is selected from the group comprising metals of the second, third and fourth main group and any subgroup of the periodic table,
x is any integer of 2 or 3; and
δ is 0 to 0.1, which catalyst is essentially free of Cl, whereby preferably the catalyst is a catalyst according to an of the fourth to the seventh aspect of the present invention. As used herein a catalyst is essentially free of Cl when such catalyst is prepared without using any Cl as reacting compounds. Also a catalyst shall be deemed as essentially free of Cl if the Cl is introduced into the catalyst as impurities of the starting materials used and, preferably, if such catalyst exhibits any of the characteristics attributed to such catalyst herein, more preferably the characteristic of being moisture resistant.

According to the present invention the problem is solved in a ninth aspect by the use of an amorphous metal fluoride of the formula $M^{x+}F_{x-\delta}$ whereby
M is selected from the group comprising metals of the second, third and fourth main group and any subgroup of the periodic table,
x is any integer of 2 or 3; and
$\delta$ is 0 to 0.1, or of a metal fluoride of the formula $M^{x+}F_{x-\delta}$ whereby
M is selected from the group comprising metals of the second, third and fourth main group and any subgroup of the periodic table,
x is any integer of 2 or 3; and
$\delta$ is 0 to 0.1, each preferably having an active surface of about 100 to 300 $m^2/g$, preferably 180-280 $m^2/g$, which is essentially free of Cl, as catalyst.

According to the present invention the problem is solved in a tenth aspect by the use of a precursor for the manufacture of a catalyst according to the present invention, whereby the precursor or precursor catalyst contains a structure having a formula of $M^{x+}F_{(x-\delta)-y}B_y$, whereby
M and $\delta$ are as defined herein;
B is a coordinately bound group as defined herein;
x is any integer between 2 or 3; and
y is any integer between 1 and 3, whereby x–$\delta$>y;

which catalyst is essentially free of Cl.

According to the present invention the problem is solved in an eleventh aspect by the use of a catalyst according to the present invention for the catalysis of halogen exchange reactions.

In a preferred embodiment the halogen exchange reaction is an exchange reaction of chlorocarbons, chlorofluorocarbons or hydrofluorocarbons.

According to the present invention the problem is solved in a twelfth aspect by the use of a catalyst according to the present invention for the catalysis of any reaction where a Lewis acid catalyst is used.

According to the present invention the problem is solved in a thirteenth aspect by the use of a catalyst according to the present invention for the use as Lewis acid catalyst.

According to the present invention the problem is solved in an fourteenth aspect by the use of a catalyst according to the present invention for the catalysis of isomerisation of haloperfluoroalkanes.

According to the present invention the problem is solved in an fifteenth aspect by the use of a catalyst according to the present invention for the catalysis of isomerisation of olefins.

According to the present invention the problem is solved in an sixteenth aspect by the use of a catalyst according to the present invention for the catalysis of Friedel-Crafts acylation reactions.

According to the present invention the problem is solved in an seventeenth aspect by the use of a catalyst according to the present invention for the catalysis of Friedel-Crafts alkylation reactions.

The present inventors have surprisingly found that an amorphous metal fluoride or a metal fluoride having a highly distorted lattice can be prepared under nonaqueous conditions using a soft-chemistry process. Such metal fluorides have, contrary to the state of the art, a high surface area, are an X-ray amorphous solid of a strongly distorted solid state structure. Additionally, the irregularities and disorder of the structural arrangement result in a mesoporous surface. Also, such metal fluorides are strong Lewis acids in case of Lewis acidic metals. These structural effects display in case of Lewis acidic fluorides, as e.g. $AlF_3$ but not limited thereto, improved catalytic properties for a variety of halogen exchange reactions, dismutations and isomerisations of CFCs/HCFCs as well as Friedel-Crafts alkylations and acylations, respectively. While the less or non-acidic metal fluorides, e.g. $MgF_2$, $CaF_2$, etc., may be used as inactive chemically inert supports or matrices in aggressive fluorination processes or in host-guest systems, the stronger Lewis acids $AlF_3$, $CrF_3$, $FeF_3$, and others are outstanding with their acidic that is catalytic properties and they are particularly preferred for industrial fluorination processes.

Such amorphous metal fluoride which is referred to herein as the metal fluoride according to the present invention, has the general formula whereby
M is selected from the group comprising metals of the second, third and fourth main group and any subgroups of the periodic table,
x is an integer of 2 or 3 and
$\delta$ is 0 to 0.1.

In case of, e.g., aluminium trifluoride having this kind of amorphous structure, it was found that it is an extremely strong Lewis acid comparable with the strongest known Lewis acids such as $SbF_5$ and ACF. As used herein and if not indicated to the contrary, amorphous metal fluoride is the same as highly distorted metal fluoride. The amorphous metal fluoride according to the present invention is X-ray amorphous. X-ray amorphous, as described herein, means that the microcrystalline domains of the solid matter, i.e. the amorphous metal fluoride, have a size of less than 20 nm. A transmission electron microscopic (TEM) study confirmed at a magnification of $10^7$ that the amorphous metal fluoride according to the present invention such as $AlF_3$, is present as very small solid particles which are partially agglomerated to form bigger units. Further electron microscopic studies (REM) revealed a mesoporous surface of the amorphous metal fluoride according to the present invention. The extensive structure and the pore structure of the amorphous metal fluoride according to the present invention result in a significant increase of the catalytic active surface and thus of the catalytic activity. BET measurements using $N_2$ as known in the art as determined, e.g., with a micromeritics ASAP 2001 machine at 77 K resulted in values of >200 $m^2/g$. Also solid state NMR studies of the central Al atom as further detailed in the examples, can be used to describe the short-range order at the aluminium and to discriminate between various Al species. A chemical shift of the resonance signal could be found at a range of δ=−12.5 to −14.5 ppm, preferably δ=−13,8 ppm, which indicates that the amorphous $AlF_3$ is present in an octrahedral orientation. From the quadrupole coupling constant QCC of about 1.5 MHz which was estimated from the satellite transitions of the spectrum, a strongly distorted structure of the $AlF_3$ octahedron could be found. These disorders of the $AlF_3$ lattice are responsible for the X-ray amorphous condition of the solid matter, i.e. the amorphous metal fluoride according to the present invention, as well as for the desired and intended increase in its catalytic activity. The seriously distorted lattice structure of the amorphous metal fluoride according to the present invention is also confirmed by IR spectroscopic studies. In case of $AlF_3$ IR spectra no absorption bands could be found beyond a wave number of 700 $cm^{-1}$. Rather only a single, very broad band (valence vibration $v_3$ of Al—F at 667 $cm^{-1}$) could be observed corresponding to the amorphous rather than the crystalline structure. The experimental proof of an increased Lewis acidity can be provided by pyridine adsorption and $NH_3$-TPD as described in the art.

Without wishing to be bound by any theory, it seems that the amorphous structure of the metal fluoride is critical to the observed catalytic activity as, for example, in case of amorphous $AlF_3$, by heating the metal fluoride to temperatures of more than 600° C. the catalytically active amorphous metal fluoride is converted into a crystalline aluminium fluoride, in case of $AlF_3$ into α-$AlF_3$, going along with a loss of its catalytic activity.

The amorphous metal fluoride according to the present invention, i.e. the catalyst according to the present invention, is industrially applicable with regard to the fact that it is in contrast to ACF as described in the introductory part resistant to moisture which thus allows regeneration of the amorphous metal fluoride and the catalyst, respectively, upon a certain time of exposure. In other words the catalyst according to the present invention is a recyclable catalyst.

It is to be noted that, in principle, the metal fluoride may also be a mixed metal fluoride such that the catalyst is a doped catalyst. The metal component of the metal fluoride and the catalyst, respectively, is preferably any divalent or trivalent metal and transition metal, respectively. Preferably, the metal component is selected from the group comprising Zn, Sn, Cu, Fe, Cr, V, Mg, and Al, whereby any of said metals may either alone or in combination be used as the independent fluoride compound, as guest component or as host component and respective compound. In a further preferred embodiment, the metal component may be Fe, Cr, V, Mg or Al, whereby any of said metals may either alone or in combination be used as the independent metal fluoride, as the guest compound or the host compound. In any of these embodiments, Mg is a preferred host compound in case of doped catalysts. In a further preferred embodiment the metal component is Mg, either as independent metal fluoride or preferably as a host component for other metal fluorides, preferably those mentioned herein. In a further embodiment Al is used as an independent metal fluoride or as host component or as guest component. Most preferably the metal component is Al, either as an independent fluoride or as host component or as guest component as used in connection with the catalyst according to the present invention. As used herein the term independent metal fluoride is meant to be the catalytically active metal fluoride, the guest compound or guest component is meant to be the doped component or compound of a doped catalyst and the host compound or host component is meant to be the matrix for the guest compound or guest component in case of doped catalysts, whereby the host compound or host component can be either an inert or a catalytically active matrix.

The present inventors have also surprisingly found that the catalyst according to the invention can be manufactured using a non-aqueous synthesis route. The respective method can in principle be divided into two steps. In the first step a solid, partially fluorinated metal compound which is going to provide the metal component of the amorphous metal fluoride, is prepared which is highly distorted because of the presence of bulky groups in stoichiometrical quantities, and which is in the second step consequently fully fluorinated under soft conditions, i.e. at a temperature below the crystallisation temperature of the respective metal fluoride to be synthesized, to preserve the distortion. Preferably, the partially fluorinated metal fluoride or the starting material thereof is a metal organic compound. As in case of the sol-gel synthesis of metal oxides the final removal of a coordinatively bound group such as alkoxide, enolate or salts of carboxylic acids from the precursor catalyst is crucial for the development of the specific morphological properties. In said subsequent second step the final fluorinating treatment of the only partially fluorinated precursor catalyst as obtained from the first step of the method is performed.

More particularly, the metal organic compound, which is preferably a salt, is at least partially dissolved in an organic solvent free of water. In a subsequent step, again free of water, anhydrous hydrogen fluoride is reacted with said metal compound. Preferred metal compounds used in this reaction are alkoxides, enolates and salts of short chain carboxylic acids of the respective metals. Preferably said short chain carboxylic acids have a length of 1 to 5 carbon atoms. A further prerequisite for the use of said carboxylic acids is that they are also used in a moisture-free manner. The amount of hydrogen fluoride used in this reaction shall be such that almost all of the organic residues or ligands bound by the metal component of the amorphous metal fluoride according to the present invention shall be replaced. Accordingly, a nearly stoichiometrical quantity of or even an excess of hydrogen fluoride is to be used. Such excess may be up to 1.5 times the amount of hydrogen fluoride required for stoichiometrical reasons. Anhydrous organic solvents as used herein are alcohols, ethers, ketones and alkanes, petroleum ether, formic acid, acidic acid and propionic acid, preferably alcohols of the formula $C_cH_{2c+1}OH$, with c being any integer from 1 to 6, preferably from 1 to 3.

In a further step all or most of the volatile compound(s) is/are removed, preferably under vacuum, giving a solid which contains to a certain extent the organic compound used as metal organic starting material. The presence of this compound obviously interferes with the forming of a regular crystalline structure thus creating the amorphous metal fluoride according to the present invention. In a still further step the thus obtained solid is treated under mild fluorination conditions. Preferably, this treatment occurs at an increased temperature which, however, is below the crystallisation temperature of the metal fluoride. Preferred temperature ranges are thus equal to or less than 350° C., less than 200° C., and less than 100° C. The organic compound is thus nearly quantitatively removed with a carbon content of preferably less than 1%, from the amorphous metal fluoride and further increases the degree of fluorination of the metal to the respective stoichiometrical ratio or close thereto. The fluorination treatment of the above mentioned solid can be done with $CH_gCl_hF_{4-g-h}$ or with gaseous HF, depending on the metal fluoride system.

The gaseous HF is used diluted with an inert gas as e.g. $N_2$ or others or in pure undiluted form at a temperature in the range between 50-300° C., preferably at 75-150° C. The HF partial pressure is in the range of 50-1500 mbar, preferably at 350-600 mbar. The fluorination of the precursor catalyst takes place in the metal reactor tube of the reaction facilities as flow reaction. This type of post fluorination is particularly preferred in cases where medium Lewis acidity is aimed.

The thus obtained catalytically active solid maintains the X-ray amorphous structure and exhibits a very large specific surface and a distorted structure compared to the crystalline form of the respective metal fluoride. This distortion is responsible for the observed tremendously high Lewis acidity of Lewis acid metals as contained in the amorphous metal fluoride according to the present invention.

It is to be noted that the method for the manufacture of the catalysts according to the present invention as described herein is also applicable to other metal fluorides contained in the respective groups of compounds, particularly Al, Cr, Fe, V, Ga and Mg, Zn, respectively, given the isotypic character of the metal fluorides within the respective, and more particularly in said two groups. Accordingly, the method of manufacture as described herein in more detail in the examples related to amorphous $AlF_3$ is also applicable, among others, to corresponding fluorides of Cr, Fe, V, and Ga, and the method for the manufacture of $MgF_2$ is also at least applicable to the corresponding fluorides of Zn.

The catalytically active metal fluorides according to the present invention are applicable in any reaction where the metal fluorides of the state of the art may be used. More particularly, the catalytically active metal fluorides may be used for the catalysis of halogen exchange reactions, whereby exchange reactions of chlorocarbons, chlorofluorocarbons or hydrofluorocarbons are particularly preferred. Also, the catalytically active metal fluorides may be used in any catalysis where a Lewis acid catalyst is used. Further preferred reactions which may be catalysed using the catalytically active metal fluorides according to the present invention are the isomerisation of haloperfluoroalkanes, whereby the haloperfluoroalkanes are preferably selected from the group comprising chloro/bromo-fluoroethanes and -propanes, for the isomerisation of olefins, whereby the olefin isomerisation is preferably selected from the group comprising alkenes-1 to alkenes-2 as e.g. butene-1 to butene-2 isomerisation, for the catalysis of Friedel-Crafts acylation reactions, whereby the acylation reactions are preferably those selected from the group comprising benzoylation/ethylation of activated as well as deactivated aromatic systems, as well as Friedel-Crafts alkylation reactions, whereby the alkylation reactions are preferably selected from group comprising the alkylation of aromatic rings.

The invention is now further illustrated by the figures and examples from which further features, embodiments and advantages may be taken, whereby.

EXAMPLE 1

Manufacture of a Catalyst Containing Amorphous $AlF_3$

Firstly, aluminium triisopropoxide ($Al(O^iProp)_3$) (10 g) was reacted in water free isopropanol (50 ml) with a moderate excess of anhydrous hydrogen fluoride dissolved in isopropanol or diethyl ether with the solution being 26 molar, under agitation and cooling. The reaction was agitated for another 1.5 h at room temperature. After removing all volatile material at elevated temperature (70° C.) in vacuum a white powdery solid remained, particularly after maintaining the reaction for another 4 h at the same conditions. Thus the precursor of the aimed aluminium fluoride was obtained. The precursor had a ratio of fluorine to aluminium of about two, and a carbon content of about 30%. Thus, despite having reacted the $Al(O^iProp)_3$ with an excess of HF, there was obviously some isopropylate together with some coordinatively bound isopropanol in the compound.

The second step in the manufacture of amorphous $AlF_3$ comprises the treatment of the precursor with a fluorinating agent such as $CCl_2F_2$ at, e.g., 350° C., i.e. below its crystallisation temperature, to remove the organic compound(s) by replacing it partially by fluorine. More particularly, a heatable Ni tube was used and the previously obtained white powder was reacted with a mixture of $CCl_2F_2/N_2$ (1:5) for 2-3 h at a maximum temperature of 350°. The final product obtained had a ratio of fluorine to aluminium of three and the carbon content was less than 0.5%.

Most strikingly, the aluminium fluoride prepared this way had a surface area of about 200 $m^2/g$ and showed a very high Lewis acidity and subsequent catalytic activity. Because of its high specific surface said aluminium fluoride was denoted HS—$AlF_3$ by the present inventors.

Figure 1:
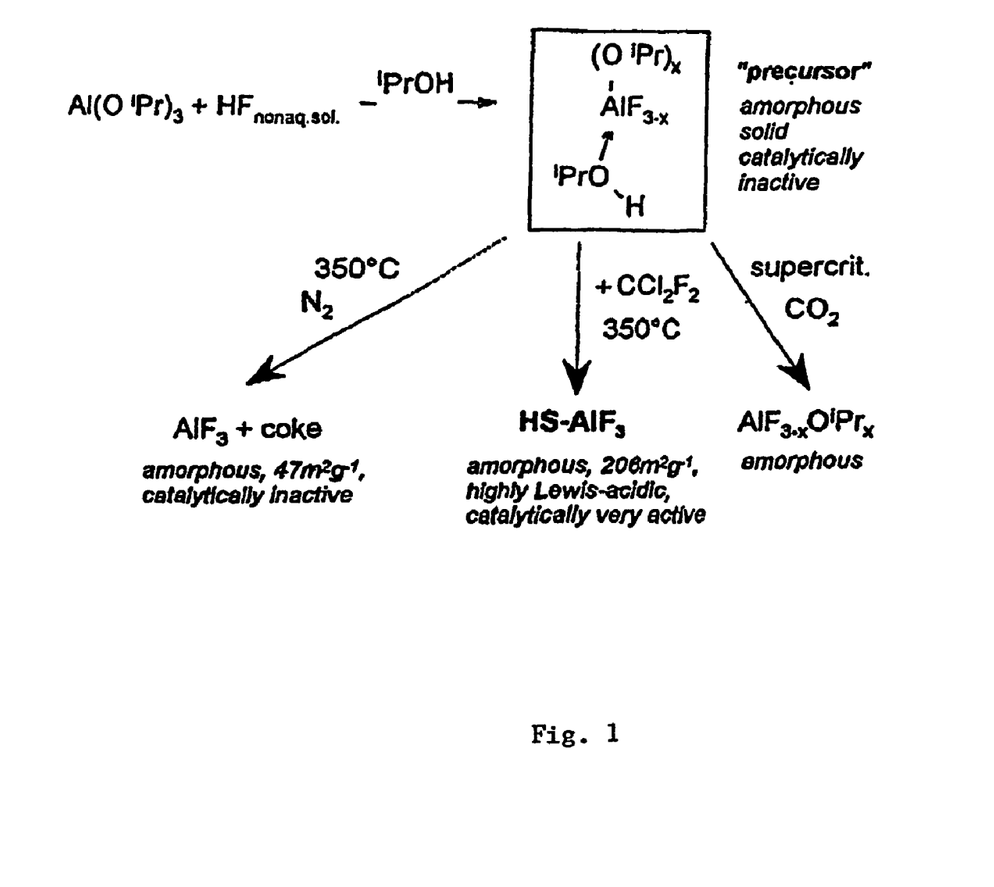
FIG. 1 shows the scheme for the synthesis of an amorphous $AlF_3$ catalyst.

Attempts to remove the organic from the precursor by supercritical $CO_2$ failed in that more than two third of the organic remained. In contrast, heating the precursor in a nitrogen flow up to 350° C. resulted in an amorphous product with only 1% carbon content and a BET-surface area of 47 $m^2/g$, which was not catalytically active. The starting materials, reaction conditions and respective products are schematically depicted in FIG. 1. These results together with the elemental analysis indicate that the precursor catalyst has a composition corresponding to the formula $AlF_{3-x}(O^iPr)_x(^iPrOH)_y$, with $x\approx1$ and $y<1$. Whereas the loosely bound alcohol can already be removed by supercritical $CO_2$, the alkoxy groups can be rather gently removed by a soft fluorination under preservation of the high morphological disorder. Hence, the presence of alkoxy groups in the precursor is decisive for obtaining high surface areas metal fluorides.

EXAMPLE 2

Manufacture of a Catalyst Containing Amorphous $MgF_2$

Basically, similar to the reaction and reaction conditions described in example 1 amorphous $MgF_2$ was produced. More particularly, Mg methylate was dissolved in isopropanol and reacted with 2.2 mole hydrogen fluoride per 1 mole Mg under cooling and stirring. The mixture was stirred at room temperature for another 60 min and then treated as described for $AlF_3$ in example 1. The precursor catalyst was then fluorinated using $CCl_2F_2$. The $MgF_2$ obtained was X-ray amorphous and had a specific surface area of 190 $m^2/g$.

EXAMPLE 3

Manufacture of a Vanadium (III) Fluoride Doped Amorphous $MgF_2$ Catalyst

A solution of 0.015 mole vanadium (III) fluoride in isopropanol was added to a solution of 0.085 mole Mg methylate in isopropanol. 0.24 mole hydrogen fluoride dissolved in diethylether is added to the previously prepared solution under agitation and exclusion of moisture. The thus obtained mixture is treated as described in example 1, whereby any of the volatile compounds are withdrawn under vacuum at a temperature between 30 and 70° C. and the remaining solid is fluorinated in a stream of $CCl_2F_2$ at a temperature rising from 30 to 350° C. over a period of 3 hours. The thus obtained metal fluoride mixture is X-ray amorphous, exhibits a specific surface of 115 m²/g and fiercely catalyses the reaction of tetrachloroethylene with HF.

EXAMPLE 4

Manufacture of a Fe doped $MgF_2$ Catalyst

In a manner analogous to the method described in example 3 an Fe doped $MgF_2$ catalyst having a specific surface of 105 m²/g is obtained using Fe (III) chloride and Mg methylate as starting material. The degree of doping of the catalyst is 15% $FeF_3$. According to X-ray analysis the host $MgF_2$ support is in a crystalline form whereas the doped $FeF_3$ is in an amorphous form. The catalyst is activated using CFC at 350° C. The carbon content of the catalyst is 0.4% and the ratio F/Al is 3. The BET/$N_2$ surface is 105 g/m².

The thus produced catalyst was used for the following two reactions:

a) Benzoylation of anisole 373 mg benzoyl chloride were reacted with 12 ml anisole and 200 mg of the above prepared catalyst at 60° C. for 3 hours. 50 mg dodecane were added to the reaction mixture as internal standard for quantitative GC analysis. The conversion was 100%, the yield of methoxybenzophenone was 72.4%.

b) Acetylation of anisole

Using the same reaction conditions as described in a) above a conversion of 46% was obtained with the yield of 4-metoxyacetophenone of 35%.

EXAMPLE 5

Manufacture of a Fe Doped $MgF_2$ Catalyst (HF Treated)

1.0 g of a Fe doped $MgF_2$ catalyst having 15% Fe/85% Mg and which was prepared from the respective metal methoxides by HF fluorination in the solvent, were first pre-treated with $N_2$ (8 cc/min) at 150° C. for 1 h, then post-fluorinated with gaseous diluted HF (5 cc/min)/$N_2$ (8 cc/min) at 120° C. for 2 h to remove residual solvent and completely fluorinate the remained alkoxide groups bound to the metal. After the post fluorination treatment the catalyst is in the amorphous state and the carbon content of the catalyst is 1%, the chlorine content yields to about 0.4%. The surface area is 243 m²/g.

The gas phase dismutation of CFC 12 according to gives conversion of 80% at 350° C.

The thus produced catalyst was used for the benzoylation of anisole with 15% Fe/Mg (HF): The reaction is run in a manner analogous to that described in example 4 with 200 mg of catalyst, 373 mg benzoyl chloride, 11 ml anisole at 60° C. for 3 hours. The results are as follows:

Conversion to MBPh: 69% Selectivity: 60%

To show that the catalyst may be re-used, further runs of the reaction were carried out. The second run of the used catalyst after washing with ethanol and drying at 100° C. and using 174 mg catalyst, 331 mg benzoyl chloride and 9 ml anisole gave the following results:

Conversion: 81% Selectivity: 68%

A third run with the reused catalyst using 122 mg catalyst, 229 mg benzoyl chloride and 7 ml anisole gave the following results:

Conversion: 45% Selectivity: 52%

EXAMPLE 6

BET/$N_2$ Surface Properties of Amorphous $AlF_3$

A comparison of the BET/$N_2$ surface properties of the aluminium fluoride according to the present invention (HS—$AlF_3$) and of its precursor with those of β-$AlF_3$, a common well-known $AlF_3$-type, which is often used as Lewis-acidic catalyst in fluorine chemistry, reveals outstanding properties. The specific surface area of β-$AlF_3$ is 33 m²/g only; treatment with $CCl_2F_2$ at 350° C. did not improve that value, compared to a specific surface are of 206 m² µg of the new active HS—$AlF_3$ and even higher values for the precursor as also depicted in table 1.

TABLE 1

Properties of Selected Aluminium Fluorides

| Sample | Crystallinity | $S_{BET}$ [m²/g] | F/Al-Ratio | C-Cont. [%] |
|---|---|---|---|---|
| Precursor | amorph. | 430 | ≈2 | 31 |
| HS-$AlF_3$ | amorph. | 206 | 3 | 0.4 |
| β-$AF_3$ | crystall. | 33 | 3 | n.a. |
| $AlF_3$ via aq. route[1] | crystall. | 113 | 3 | 0.15 | n.a. not applicable;
[1] treated with $CCl_2F_2$ at 350° C.

EXAMPLE 7

Morphological Characterization of a Catalyst Containing Amorphous $AlF_3$

Figure 2:
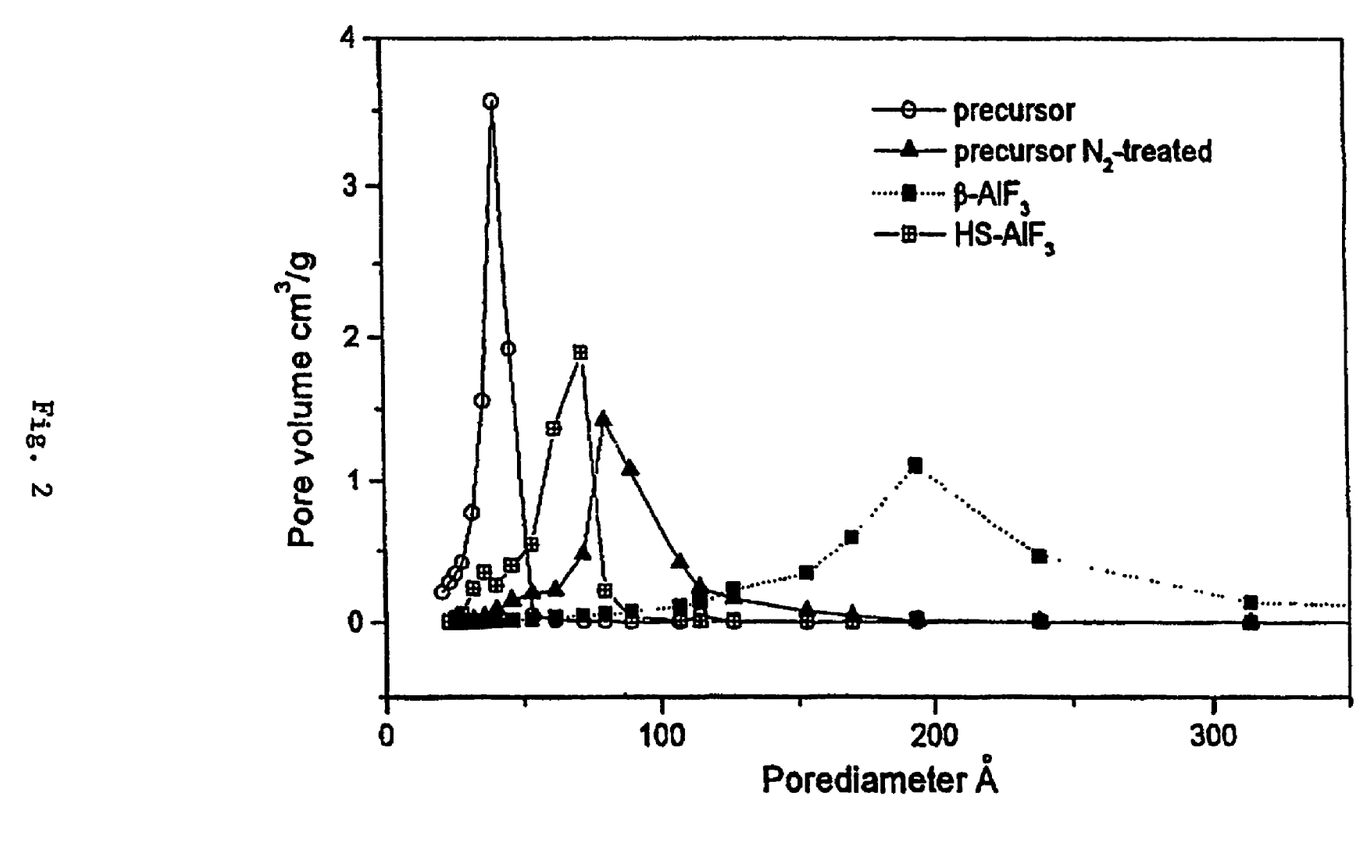
FIG. 2 shows a diagram depicting the pore volume as a function of the pore diameter of various $AlF_3$.

In order to further characterize the inventive catalyst as represented by a catalyst comprising $AlF_3$, the pore-size distribution was determined of both the precursor catalysts as well as the $AlF_3$ catalysts according to the present invention. As can be taken from FIG. 2 the amorphous $AlF_3$ catalyst has a much narrower pore-size distribution than β-$AlF_3$.

In addition, SEM micrographs show that the amorphous HS—$AlF_3$ according to the present invention as well as its precursor is composed of mesoporous particles, most probably of agglomerates of much smaller particles, of irregular size. TEM micrographs (magnification $1.5 \times 10^6$ fold) of single agglomerates show well-defined domains some of which are regular, i.e., lattice planes can be seen of regions which are, however, too small to be detected by XRD. Energy-dispersive X-ray spectroscopy (EDX) confirms the elemental analysis of the HS—$AlF_3$ to consist of Al, F and some O after the fluorination/activation treatment. Oxygen most likely results from surface hydration when the solid is handled in open atmosphere. This is also in agreement with data of XPS-spectra.

EXAMPLE 8

NMR- and IR-Spectra of a Catalyst Containing Amorphous $AlF_3$

To get deeper insight into the structural situation of the HS—$AlF_3$ according to the present invention, IR- and $^{27}Al$-MAS-NMR-spectra of the solid were recorded. The latter allow to describe the short-range order at Al atoms and to discriminate between different Al species. $^{27}Al$-MAS-NMR-spectra were collected at 132.2 MHz at a spinning rate of 10 kHz. The observed chemical shift of δ=−13.8 ppm is indicative of an octahedral surrounding of Al sites of a polymorphous solid. As compared with crystalline aluminium fluoride, e.g. α-$AlF_3$, the chemical shift underlines a tendency to a lower field resonance, i.e., towards coordinatively unsaturated species.

The large sideband manifold of the satellite transitions of the quadrupolar Al nucleus in respective spectra indicates large quadrupole coupling constants QCC of Al sites, consistent with stronger distortions of the octahedral environments. Clear discontinuities due to 1st order QCCs were not found because of wide distributions of the QCCs. Sideband simulations point at QCC of about 1.5 MHz which is much larger than that of the highly symmetric α-$AlF_3$, but comparable with the estimated 1.4 MHz of the nearly amorphous material as described in J. L. Delattre et al., J. Am. Chem. Soc. 2001, 123, 5346.

The IR-spectra of the HS—$AlF_3$ according to the present invention support these findings. There should be no absorption bands for $AlF_3$ above 700 cm$^{-1}$. In fact, only one band at 667 cm$^{-1}$ (Al—F valence vibration $v_3$) could be seen, which was very broad due to the amorphous state of the compound. Complementary attempted Laser-Raman analysis was not successful because of fluorescence phenomena, obviously due to the carbon present. The chemical surface properties of the HS—$AlF_3$ are reflected by its pyridine absorption and more important by its catalytic properties. After treatment with pyridine and subsequent heating in a $N_2$ stream at 150° C. the photoacoustic IR-spectra of the solid showed strong bands at 1454 and 1492 cm$^{-1}$ indicating strong Lewis- as well as Brønsted-acid sites. The latter might have resulted from reaction of strong Lewis-sites with moisture because contact to air could not be excluded during the sample preparation for photoacoustic measurements.

EXAMPLE 9

Catalytic Activity of a Catalyst Comprising Amorphous $AlF_3$

The catalytic activity was investigated in comparison to the precursor, to β-$AlF_3$, and to an amorphous $AlF_3$ prepared conventionally from aqueous $AlF_3$ solution and subsequent $CCl_2F_2$ treatment at 350° C. As test reactions the temperature dependence of catalytic $CCl_2F_2$ dismutation and the catalytic isomerisation of 1,2-dibromohexafluoropropane to 2,2-dibromohexafluoro-propane were studied (table 2). It may be taken from table 2 that the latter reaction, which has otherwise to be catalysed by the strongest known Lewis acids (SbF$_5$ or ACF), proceeds with the HS—$AlF_3$ according to the present invention nearly quantitatively, too. However, and in striking contrast to ACF, HS—$AlF_3$ is not destroyed by contact with moisture, but it can be reactivated by heating. Thus, it is suited for industrial application.

TABLE 2

Catalytic Activity of Selected Aluminium Fluorides

| Sample | $CCl_2F_2$ Dismutation [%] at Temp. [° C.] | | | $C_3Br_2F_6$ Isomerisation [%] at 25° C. |
|---|---|---|---|---|
| | 300 | 200 | 100 | |
| Precursor | 0 | 0 | 0 | 0 |
| HS-$AlF_3$ | 96 | 87 | 22 | 90 |
| β-$AlF_3$ | 93 | 47 | | 0 |
| $AlF_3$ [1] | 96 | 28 | 11 | 5 |

[1] via aq. route, treated with $CCl_2F_2$ at 350° C.

EXAMPLE 10

Alkylation of Benzene 8.9 ml of benzene were reacted with 0.8 g iso-propylchloride in a batch process in the presence of 0.3 g of a heterogeneous catalyst according to the present invention, consisting of a high surface area $AlF_3$ on alumina as support. The catalyst system $AlF_3/Al_2O_3$ is used without any kind of activation. After stirring the mixture for 0.5 hours at room temperature the reaction was finished. Iso-propylbenzene as the reaction product is identified with an authentic sample by GC. Conversion of 74% yield was found with a selectivity of 52%. For comparison reasons: no conversion took place using a conventionally prepared $AlF_3$ catalyst instead. GC conditions are as follow: wide pore quartz column, 15 m length, DB5 polysilixane modi-fied, internal standard dodecane.

EXAMPLE 11

Benzoylation of Anisole 370 mg of benzoylchloride were reacted with 12 ml anisole to give the benzoylated product 4-methoxybenzophenone in 47% yield. The catalyst used is a HS—$AlF_3$ metal fluoride on a $Al_2O_3$ support prepared according to the present invention, which is used in an amount of 300 mg. The reaction is carried out in a discontinuous batch process at 60° C. under reflux with stirring.

When using a conventionally prepared $AlF_3$ catalyst no reaction occured, GC yield 0%.

Products and yields were estimated by GC. Internal standard is tridecane.

EXAMPLE 12

Hydrofluorination of Tetrachloroethylene $C_2Cl_4$

In a flow reactor 300 mg of the supported catalyst according to the present invention (15% $FeF_3$ on $MgF_2$) with a BET-surface area of 102 m$^2$/g were pre-treated in situ at 300° C. under $N_2$ for 0.5 hours, afterwards with a BF/$N_2$-gas mixture at 400° C. The catalytic reaction was investigated by passing through a $N_2$ stream saturated with tetrachloro-ethylene vapour along with gaseous HF at 360° C. reaction temperature. Conversion at this temperature amounts to 74% giving a mixture of freons R123, R124, R125 and a small amount of others. The hydrofluorination reaction was also studied at 280° C. and 320° C. (see table below).

Products were analysed by GC-FD with a 10% SE Chromosorb column.

| T ° C. | conv. % | $C_2HCl_2F_3$ % | $C_2HClF_4$ % | $C_2HF_5$ % | others |
|---|---|---|---|---|---|
| 280 | 50 | 23 | 11 | 3 | 13 |
| 320 | 66 | 11 | 41 | 13 | 2 |
| 360 | 74 | 6 | 29 | 37 | 2 |

EXAMPLE 13

Chromium Doped Magnesium Fluorides

The doping of magnesium fluoride by chromium is achieved by 3 different compounds and the respective routes: i) Cr(III)Cl$_3$, ii) basic chromium acetate Cr$_3$Ac$_7$(OH)$_2$ and iii) CrO$_3$/methanol.

To a slurry of magnesium methoxide in methanol the appropriate amount of a chromium (III) compound, dissolved in dry ethanol, was added. The obtained mixture was in the first step fluorinated with the stoichiometric amount of HF dissolved in water-free diethylether. The solvents were removed by evacuation and the remaining solid was post-fluorinated in an activation step at temperatures up to 350° C. with a CFC as e.g. CF$_2$Cl$_2$. According to route iii) the Cr(VI) oxide was prior to the mentioned pathway reduced to the oxidation state (III) by reacting with methanol.

The concentration of chromium in atom % in the different doped catalysts varies between 8% and 40%. Diffraction pattern of the solids show that all samples are essentially amorphous. Weak reflections in X-ray diffraction (XRD) are due to the host material. The BET surface area is high and in the range of 100 to 175 m$^2$/g with the only exception of the ii) product with only 65 m$^2$/g. The carbon content in the precursor amounts from 3 to 12%, and after the post fluorination step it is in the range of about 0.1 to 0.9%. The strength of Lewis acid sites is verified by FT-IR photoacoustic pyridin adsorption.

Catalytic tests were evaluated in dismutation reactions of dichlorodifluoromethane (R 12) and chlorotetrafluoroethane (R 124) as well as with the hydrofluorination of tetrachloroethene (TCE) by HF. All reactions were run as gas phase reactions in a flow reactor made of nickel with of 0.3 to 0.6 g of catalyst. The gas flow was adjusted by mass flow meter.

In R 12 dismutation highest yields were found for the iii) 15% Cr doping with 15% conversion at 100° C.; 65/200; 85/250 and 81% at 350° C. The 8% doped catalyst of this type showed similar results. The 40% ii) was efficient as well with conversion of 57% at 300° C. and 78% at 350° C. The R 124 dismutation reaction, analysed by F-NMR and GC-MS of the collected products condensed in a cold trap, gave best results with 8% Cr-content of iii). Conversions are 35% at 150° C., 48/200, 86/250 and 94% at 300° C. Hydrofluorination of TCE gave lower yields: 7% at 320 and 18% at 360° C. for the 40% Cr— ii) catalyst.

The features of the present invention disclosed in the specification, the claims and/or the drawings may both separately and in any combination thereof be material for realizing the invention in various forms thereof.

The invention claimed is:

1. A method for preparing an amorphous metal fluoride of the formula $M^{x+}F_{x-\delta}$ comprising the steps of a) providing a precursor, whereby the precursor comprises a structure having a formula of $M^{x+}F_{(x-\delta)-y}B_y$; and b) reacting the precursor with a fluorinating agent generating the amorphous metal fluoride having a formula of $M^{x+}F_{x-\delta}$, wherein M is selected from the group consisting of metals of the second, third and fourth main group and any subgroup of the periodic table, B is a coordinately bound group;

x is any integer of 2 or 3;

y is any integer of 1, 2 or 3;

δ is 0 to 0.1; and x−δ>y.

2. The method according to claim 1, wherein B is selected from the group consisting of alkoxides, enolates and salts of carboxylic acids.

3. The method according to claim 2 wherein said alkoxides, enolates and salts of carboxylic acids have a length of 1 to 5 C atoms.

4. The method according to claim 1, wherein the precursor, the starting material for the precursor or the fluorinating agent is present in or introduced into an anhydrous organic solvent.

5. The method according to claim 4 wherein said anhydrous organic solvent is selected from the group consisting of alcohols, ethers, ketones, alkanes, formic acid, acetic acid and propionic acid.

6. The method according to claim 1, wherein the precursor contains or is made from a compound of the formula wherein M, F, x, y, δ and B are defined as in claim 1;

L is a solvent, and d is ≦1.

7. The method according to claim 1, wherein step b is carried out at a temperature below the crystallisation point of the amorphous metal fluoride.

8. The method according to claim 1, wherein the precursor is prepared by providing the metal component of the precursor as an anhydrous metal compound, and reacting said metal component with anhydrous hydrogen fluoride.

9. The method according to claim 8, wherein said anhydrous compound is $M^{x+}B_x$, wherein M is selected from the group consisting of metals of the second, third and fourth main group and any sub group of the periodic table, B is a coordinately bound group, and x is any integer of 2 or 3.

10. The method according to claim 1, wherein the fluorinating agent is $CH_gCl_hF_{4-g-h}$ with the sum of g+h being equivalent to 1 to 3.

11. The method according to claim 1, wherein the fluorinating agent is HF.

12. The method according to claim 1, wherein the amorphous metal fluoride is a catalyst.

13. A catalyst produced by a method according to claim 12.

14. An industrially producible catalyst according to claim 13, containing amorphous metal fluoride of the formula $M^{x+}F_{x-\delta}$, wherein M is selected from the group consisting of metals of the second, third and fourth main group and any subgroup of the periodic table, x is any integer of 2 or 3, and δ is 0 to 0.1, which is catalytically active and has an active surface of about 100-300 m$^2$/g.

15. The catalyst according to claim 14 which has an active surface of 180-280 m$^2$/g.

16. A moisture resistant catalyst according to claim 13, containing amorphous metal fluoride of the formula M$^{x+}$F$_{x-\delta}$, wherein
M is selected from the group consisting of metals of the second, third and fourth main group and any subgroup of the periodic table,
x is any integer of 2 or 3, and
$\delta$ is 0 to 0.1.

17. The catalyst according to claim 13, wherein M is selected from the group consisting of Zn, Sn, Cu, Fe, Cr, V, Mg and Al.

18. The catalyst according to claim 17 wherein M has a charge of +2 or +3.

19. The catalyst according to claim 13, wherein M is a guest component of the catalyst.

20. The catalyst according to claim 13 wherein M is a host component of the catalyst.

21. The method according to claim 12 wherein said catalyst is a heterogeneous catalyst.

22. A method for the manufacture of a catalyst comprising amorphous metal fluoride of the formula M$^{x+}$F$_{x-\delta}$,
wherein M is selected from the group consisting of metals of the second, third and fourth main group and any subgroup of the periodic table,
x is any integer of 2 or 3; and
$\delta$ is 0 to 0.1, comprising the steps of the method according to claim 1, wherein the amorphous metal fluoride is the catalyst.

23. An amorphous metal fluoride produced by a method according to claim 1.

24. A catalyst comprising amorphous metal fluoride of the formula M$^{x+}$F$_{x-\delta}$,
wherein M is selected from the group consisting of metals of the second, third and fourth main group and any subgroup of the periodic table,
x is any integer of 2 or 3; and
$\delta$ is 0 to 0.1,
which is catalytically active and has an active surface of about 100-300 m$^2$/g.

25. A catalyst according to claim 24 containing a metal fluoride of the formula M$^{x+}$F$_{x-\delta}$, wherein
M is selected from the group consisting of metals of the second, third and fourth main group and any subgroup of the periodic table,
x is any integer of 2 or 3; and
$\delta$ is 0 to 0.1,
which catalyst is essentially free of Cl.

26. The catalyst according to claim 24 which has an active surface of 180-280 m$^2$/g.

* * * * *